United States Patent [19]

Legrand

[11] Patent Number: 4,676,799
[45] Date of Patent: Jun. 30, 1987

[54] PROSTHESIS FOR REPLACEMENT OF THE HIP'S JOINT

[75] Inventor: Raymond Legrand, Etampes, France

[73] Assignee: Richards Medical France, S.A.R.L., France

[21] Appl. No.: 786,230

[22] Filed: Oct. 9, 1985

Related U.S. Application Data

[63] Continuation of Ser. No. 563,312, Dec. 20, 1983, abandoned.

[30] Foreign Application Priority Data

Dec. 20, 1982 [FR] France ................. 82 21347

[51] Int. Cl.[4] ........................... A61F 2/34; A61F 2/30
[52] U.S. Cl. ........................................ 623/22; 623/18
[58] Field of Search ................................. 623/16-23; 128/92 C, 92 CA

[56] References Cited

U.S. PATENT DOCUMENTS 4,031,570  6/1977  Frey ........................................ 623/21
4,172,296 10/1979  D'Errico .................................. 623/21

Primary Examiner—Richard J. Apley
Assistant Examiner—David J. Isabella
Attorney, Agent, or Firm—Pravel, Gambrell, Hewitt & Kimball

[57] ABSTRACT

A prosthesis for the replacement of the hip including a femoral part (10) ended by a spherical head (20) and a cup (22) having an external shell (22) designed to be fitted into the acetabulum cavity (38) and containing a cap connected to the shell. A circumferential throat (28) for collecting synovial fluid is formed between the hemispherical surface (26) of the cap and the opening through which the head is inserted.

7 Claims, 3 Drawing Figures

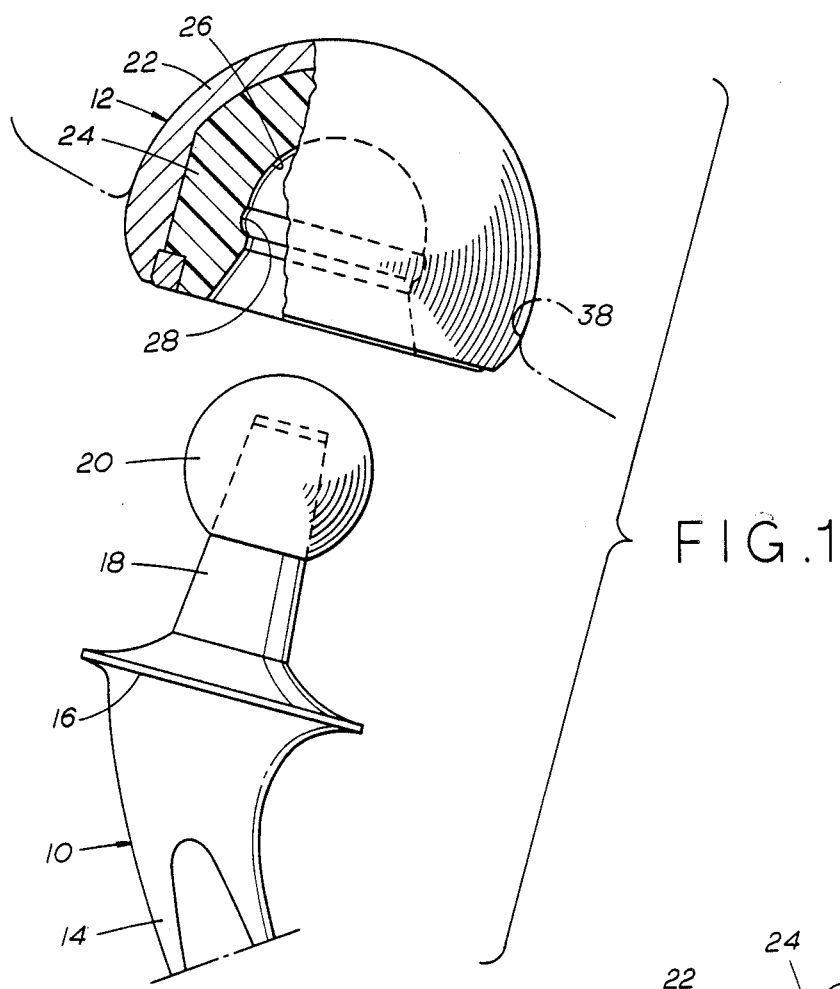
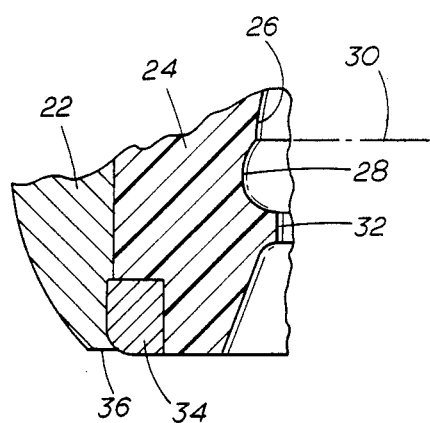
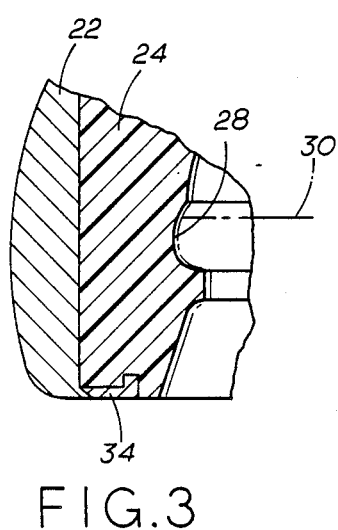

PROSTHESIS FOR REPLACEMENT OF THE HIP'S JOINT

This is a continuation of application Ser. No. 563,312 filed Dec. 20, 1983, now abandoned.

BACKGROUND OF THE INVENTION

The present invention concerns a partial prosthesis meant to replace the hip's joint of the type including a metallic femoral part ended by a spherical head and a cup including an external metallic shell meant to be fitted in a milled location in the acetabulum cavity and containing a cap made of synthetic material with an internal hemispheric surface receiving the head with an easy fit.

Some prostheses of this type are known, which have a shell with an external surface which is smooth and spherical to enable it to be oriented in the cavity. Such a prosthesis, with a double articulation, has a significant clearance. However, the fit on the acetabulum cartilage or even on the sub-chondral bone can cause pain, a tear or even a penetration, which is not acceptable. To avoid these problems, a prosthesis is proposed in which the female part includes a cap made of plastic, fitted in the acetabulum cavity of the hip. In order that the clearance of the joint involves only a relative movement between the cap and the head, the interior spherical surface of the cap has a diameter sufficient to allow the head a sufficient clearance so that it has a great range of movement. This clearance, which is necessary to avoid the dragging of the cap by the head, is far from being without problems, the point of articulation not being fastened. In addition, such a cap presents a phenomenon of flow relatively fast, often called in English "cold flow," which results in a rapid loss of the shape and of the characteristics of the origin of the prosthesis.

The goal of the invention is to provide a partial prosthesis to replace the hip joint, better able to meet the practical demands than those previously known, notably because of the fact that it solves the problems cited above and provides a prosthesis which moves accurately with low friction between moving surfaces and which is compatible with body tissues.

Therefore, with this goal in mind, the invention offers a prosthesis of the type above-described, which includes a circumferential throat designed to receive serous-like synovial fluid from the body. The throat is formed between the hemispherical internal surface of the cap and the opening where the head is inserted.

The synovial fluid is carried and distributed throughout the head by means of capillary action, insuring good lubrication during normal movements between the head and the cap, only an accidental displacement of a great amplitude (for example, after a fall) causing the shell to move relative to the bone.

The circumferential throat can have a very small depth, as a general rule smaller than a millimeter, considering that the collection of the synovial fluid and their distribution is accomplished through the forces of capillary action between the head and cup. This throat can be formed on the diameter of the internal surface and can have a depth of from one to a few millimeters. An internal protrusion on the cap can project inwardly beyond the throat to create a light retaining effect on the head once it is inserted. This protrusion needs to project only slightly on the introduction tract of the head, as its use is to insure the joining of the femoral part and femoral part having been locked in place and the cavity having been smoothed and calibrated in the opening which receives the cup, the surgeon reduces the chance of dislocation by forcing the head into the cup. A femoral part without such support could move out of the cup. The shape of the throat also increases the range of movement of the protrusion.

BRIEF DESCRIPTION OF THE DRAWINGS

The invention will be better understood with the reading of the following description of the modes of embodiment particular to the invention given as non-limiting examples. The description refers to the drawing accompanying it in which:

FIG. 1 is a cut-away view of the prosthesis showing the elevated femoral part and the cup in partial cross-section;

FIGS. 2 and 3 are detailed views at a larger scale, but following a plan through the cup's axis, showing several possible shapes of the throat for collecting synovial fluid.

DETAILED DESCRIPTION OF PREFERRED EMBODIMENTS

The partial prosthesis shown in FIG. 1 is made of a femoral part 10 and of a cup 12. The femoral part 10 can be considered as having a shaft 14 for the purpose of being anchored without being fastened in the diaphasis, after the amputation of the femur's head. The femoral part 10 also includes a plate 16 with a non-curling inferior face designed to bear against the resected extremity of the femur, a neck with a truncated conical shape 18 and a spherical head 20. The head 20 can be inserted on the neck 18 of the femoral part, the latter being formed of one piece by forging, then cutting. Shaft 14 is formed of several longitudinal strands (generally 4) which are joined at their free extremities to prevent them from spreading apart. However, the strands are free to slide longitudinally one in relation to the others. Such a composition of the shaft or tail of the femoral part is described in greater detail in the request for certificate of addition filed in France, Ser. No. 81 23325. This design provides a strong anchoring and gives the prosthesis an elasticity resembling the elasticity of the bone, therefore not causing resorption of the bone.

Cup 12 has on its outer surface an external metallic shell 22, which has a cap shape with an interior surface that is partially spherical, which is slightly greater than hemispherical in shape. The shell 22 is made, as is femoral part 10, of a metal having a good compatibility with the tissues such as a chrome and cobalt alloy known under the commercial name of "Vitallium," an inoxydizable steel 316L, titanium or another compatible material, for example, a composition made of carbon fibers or of glass.

The external surface of the shell is milled in a tight and polished manner and shaped to fit into a smoothed cavity in the acetabulum cartilage and inserted in a way to avoid movement in the cavity. Shell 22 supports the cap 24 which is formed of a synthetic material also compatible with the tissues (usually polyethylene of high density) and arranged coaxially to the shell. The internal cavity of cap 24 is formed as a hemispheric zone 26 to support the head 20, the zone 26 being separated from the opening through which the head 20 is introduced by a collection zone for synovial fluid. In the embodiment shown in FIGS. 1 and 2, this zone has a circumferential throat 28 which extends in an axial direction from a diametrical plane 30 of the cavity to a circumferential protrusion 32 which forms an internal diameter slightly smaller than that of the head 20. The depth of throat 28 will be relatively small, usually less than a millimeter, and its connection with the hemispheric zone 26 will be gradual to prevent blocking of the flow of the synovial fluid by corner effect. The axial width of the throat 28 will be of a few millimeters and its bottom could have a curved shape in order to have a varied depth.

As it has been indicated above, the protrusion 32 only has a secondary role and can sometimes be omitted. The difference between its diameter and the head's diameter will be small, usually not beyond some tenths of a millimeter.

To avoid the movement of cap 24, the cup of FIG. 2 has a thin retaining metallic ring 34 fitted on the terminal section of the cap. The shell 22 and the cap are joined by a metallic, thin crimping collar 36 which also resists movement.

With the help of the lubrication, there is a small clearance between the head and the cup without, however, causing the cup to rotate. The acceptable surface of the clearance is relatively high by the presence of neck 18 and the small protrusion on the cup beyond the diametrical surface 30. This design restricts a sliding of the cup in relation to the bony tissues, except under exceptional circumstances.

In the alternative embodiment shown in FIG. 3, the portion of the throat 28 located above the diametrical plane 30 has a slightly conical shape to allow synovial fluid to flow easily between the head and the cap which in turn is fixed on the shell.

By way of example, a prosthesis according to the embodiment of FIG. 1 can include one head of 25 millimeters diameter adapted for use with several cups of an external diameter ranging from 40 to 60 millimeters. A throat 28 with a maximum depth of about 3 millimeters, is located between the diametrical surface 30 and an annular protrusion 32 of 24.5 millimeters in diameter.

The formation of a cup according to the invention does not present any special difficulty. The shell is typically milled from a metal rod or a forging. The cap is also milled from a rod of appropriate plastic material. as it has been indicated above, this material is usually polyethylene. However, other materials can be use, such as polyfluorethylene or even plastics reinforced by the inclusion of fibers. The cap is then given its anticreeping ring, when such a ring is provided, then slipped and fixed in the shell.

The insertion of the prosthesis is a relatively simple operation. After amputation, the femoral shaft is prepared with the help of a perforator and of an instrument known as a Moore rasp. A flexible borer is used to create a spiking of the femur, at a diameter slightly smaller than the dimension of the head. The femoral element is inserted and then driven in with hard rubbing until the plate comes to rest on the surface of the cut. If several heads having different cones are contemplated, the length of the protrusion can be adjusted to any special need.

The cavity which is formed to receive the cup is prepared with a diameter chosen in relation to the patient's skeleton. The acetabulum cartilage is removed with suitable cutters and the location adjusted, if possible, to receive a fraction of the shell going beyond the half-sphere in such manner that, because of the bone elasticity, the shell ratches itself in the cavity, while inserted.

For this, tube gauges are used which create an exact shape. The cup is placed on the femoral element, the protrusion 32 ensuring a sufficient ratching to avoid an accidental separation. Then the dislocation is reduced by inserting the cup into the compartment of the acetabulum cavity, designated as reference numeral 38 in FIG. 1. Afterward, the associated muscles and the efforts of support will keep the head 20 and cup joined together, the cone's trunk shape of the neck ensuring sufficient clearance.

What is claimed as the present invention is:

1. A prosthetic device, comprising:
   (a) a cup portion with an outer surface adapted to fit in a cavity formed in a first adjacent bone, the cup including a smooth, at least partially rounded, bearing surface;
   (b) a head connected to a connection means adapted to be fixed to a second adjacent bone, the head being at least partially rounded in shape and sized to fit closely into and engage the bearing surface on the cup;
   (c) the bearing surface including a circumferential reservoir in the vicinity of the outermost portion of the rounded bearing surface which engages the head for collecting synovial fluid which can be drawn by capillary action between the head and bearing surface for lubricating the portions of the bearing surface and head that engage each other;
   (d) the bearing surface being no greater than hemispherical in shape, the reservoir being located adjacent to the outer diametrical plane of the bearing surface; and
   (e) protrusion means provided on the bearing surface on the outer end of the reservoir, the protrusion means projecting inwardly a distance sufficient to provide a slight friction lock for maintaining the head in place.

2. The prosthetic device of claim 1, wherein the cup portion includes a truncated cone-shaped throat for communicating with the bearing surface.

3. The prosthetic device of claim 2, wherein the reservoir is formed at the intersection of the throat and bearing surface.

4. The prosthetic device of claim 1, wherein the reservoir is formed as a continuous circumferential groove.

5. The prosthetic device of claim 1, wherein the bearing surface is hemispherical in shape and the reservoir is formed adjacent to the diametrical plane of the bearing surface.

6. The prosthetic device of claim 1, wherein the protrusion means is formed continuously around the bearing surface.

7. The prosthetic device of claim 1, wherein the bearing surface is slightly less than hemispherical in shape.

* * * * *